United States Patent [19]
Aronsson et al.

[11] Patent Number: 5,697,997
[45] Date of Patent: Dec. 16, 1997

[54] METHOD AND DEVICE FOR PREPARING IMPLANT SURFACES

[75] Inventors: Björn-Owe Aronsson, Kungälv; Patrik Johansson, Göteborg; Bengt Kasemo, Mellerud; Jukka Lausmaa, Göteborg, all of Sweden

[73] Assignee: Nobel Biocare AB, Gothenburg, Sweden

[21] Appl. No.: 647,284

[22] Filed: May 9, 1996

Related U.S. Application Data

[63] Continuation of Ser. No. 162,627, Dec. 7, 1993, abandoned.

[30] Foreign Application Priority Data

Dec. 7, 1992 [SE] Sweden .................... 9203663

[51] Int. Cl.$^6$ .............. C03B 32/00; A61L 2/14; A61C 8/00
[52] U.S. Cl. .............. 65/32.1; 65/157; 422/23; 433/201.1; 623/901
[58] Field of Search ................ 65/17.1, 32.1, 65/34, 157, 374.12, 374.13, 375; 422/23, 292, 297, 300, 906; 433/173, 174, 175, 176, 201.1; 53/432, 510, 284.6; 623/901; 29/DIG. 7, DIG. 44, DIG. 45; 204/157.15, 193

[56] References Cited

U.S. PATENT DOCUMENTS

| | | | |
|---|---|---|---|
| 3,948,601 | 4/1976 | Fraser et al. | 422/23 |
| 4,330,891 | 5/1982 | Branemark et al. | 623/16 |
| 4,959,199 | 9/1990 | Brewer | 422/300 |
| 5,071,351 | 12/1991 | Green, Jr. et al. | 433/173 |
| 5,173,273 | 12/1992 | Brewer | 422/297 |
| 5,188,800 | 2/1993 | Green, Jr. et al. | 422/23 |
| 5,376,332 | 12/1994 | Martens et al. | 422/23 |

FOREIGN PATENT DOCUMENTS

| | | |
|---|---|---|
| 0 248 117 | 12/1986 | European Pat. Off. |
| 0 523 372 | 6/1992 | European Pat. Off. |
| 2 318 617 | 7/1976 | France . |
| WO 88/06459 | 9/1988 | WIPO . |
| WO 93/12821 | 7/1993 | WIPO . |

OTHER PUBLICATIONS

Patent Abstracts of Japan vol. 15, No. 126 (C–0817) 27 Mar. 1991 and JP–A–03 010 061 (Nissin Electric Co Ltd) 17 Jan. 1991 *Abstract*.

Biomaterial and implant surfaces: On the Role of Cleanliness, Contamination, and Preparation Procedures, Kasemo et al., J. Biomed. Mater. Res.: Applied Biomaterials, vol. 22, No. A2, 145–158 (1988).

Primary Examiner—Steven P. Griffin
Attorney, Agent, or Firm—Pollock, Vande Sande & Priddy

[57] ABSTRACT

A method for preparing implant surfaces using gas discharge plasma including conveying the implants to a vacuum chamber. The implants are treated with an inert gas plasma to remove existing surface contamination and oxide layers from the implant surfaces. The implants are treated with an oxidizing plasma or by means of thermal oxidation to reoxidize the implant surfaces. The implant treatment steps are carried out in a closed space, including a controlled atmosphere and produce a highly accurate and reproducible microstructure, composition, purity, and sterility in the implants.

21 Claims, 3 Drawing Sheets

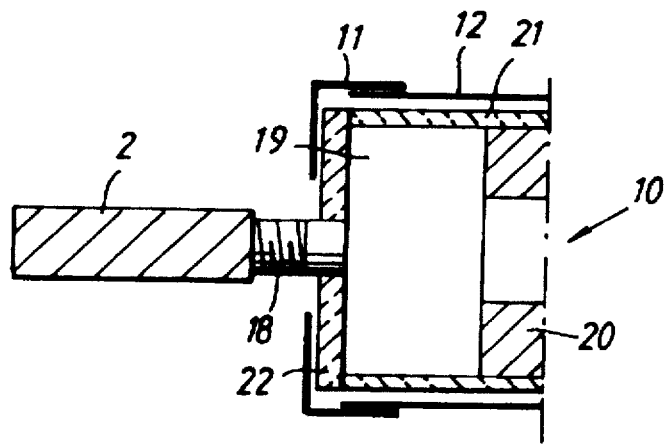
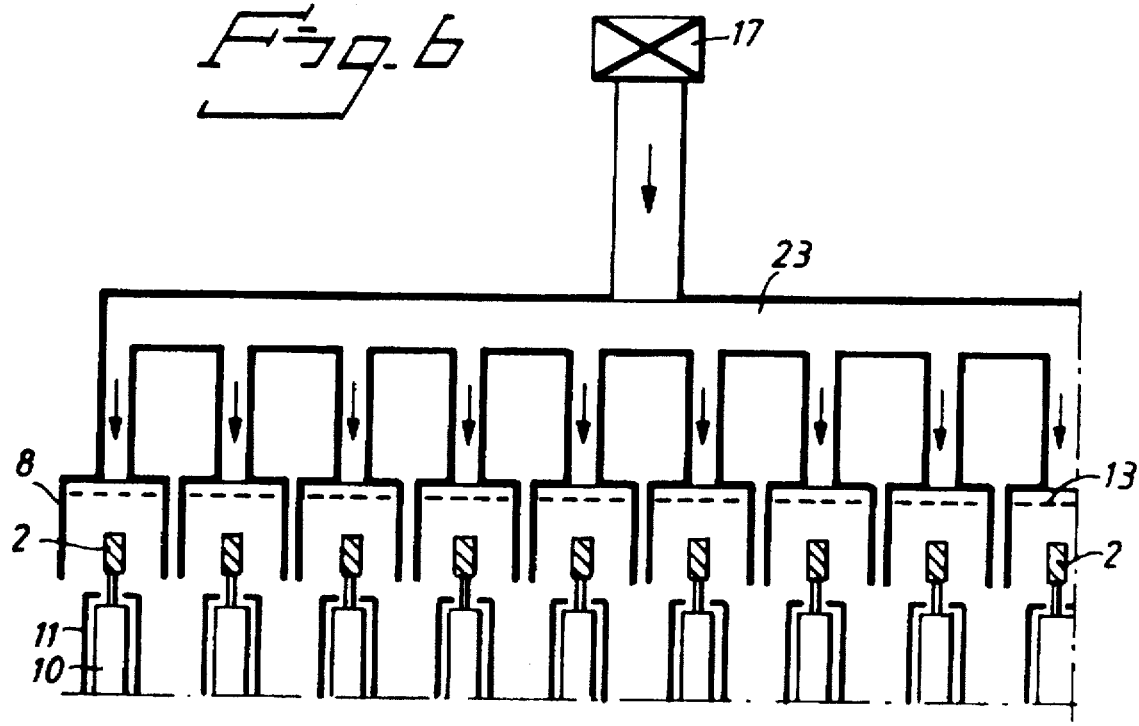

METHOD AND DEVICE FOR PREPARING IMPLANT SURFACES

This application is a Continuation of U.S. patent application Ser. No. 08/162,627, filed Dec. 7, 1993, now abandoned.

FIELD OF THE INVENTION

The present invention relates to a method and device for preparing implant surfaces of metallic or ceramic material, preferably titanium, using gas-discharge plasma with the aim of obtaining a well-defined and reproducible implant surface.

BACKGROUND OF THE INVENTION

It is previously known permanently to anchor oral and extraoral prostheses in bone tissue. In order to avoid the prostheses loosening, a healing-in period is required with direct contact, that is, exact adaptation, between the prosthesis and the bone tissue. Such an exact, enduring, adaptation permitting load-transfer is called osseointegration. That such an enduring adaptation and function can be achieved in clinical practice using load-bearing synthetic fixing elements was first demonstrated by Dr Brånemark and co-workers. They showed that screw-shaped fixing elements, so-called fixtures, of pure titanium were osseointegrated if a number of preconditions were fulfilled. The osseointegration principle developed by Professor Brånemark and co-workers has a very high success rate (more than 90%) and has been used clinically since 1965. In all, hundreds of thousands fixtures have by now been implanted throughout the world.

The osseointegration principle is based not only on the implant being executed in pure titanium, but also on a first operation in which the fixture is inserted by an atraumatic technique, a healing phase of critical length without loading, and a second operation involving attachment of a loading element, or prosthesis part. In other words, osseointegration is based, in part, on a two-session process with an intermediate healing period without loading.

For the fixture to heal well in the body tissue, it is necessary to minimize the induction of negative biological reactions, or, even better, to induce for predominantly positive reactions. The structure and chemical composition of the surface layer of the fixture have been found to be of crucial importance for these reactions.

Swedish Patent 79.02035-0 describes how improved results can be achieved by imparting a specific surface structure to the titanium-containing material in the fixture. The surface layer of the fixture consists of micro-cratered titanium dioxide, with the craters in the surface having a diameter of 10–1000 nm, preferably 10–300 nm.

The surface properties (structure and chemical composition) of the implant are, thus, important for its function since they determine how the tissue at the site of implantation will react. During manufacture of implants, therefore, continuous analyses are carried out to check that the surfaces of the components fulfil a given specification, with regard, among other things, to microstructure, composition, purity and sterility. It is, thus, desirable that the production methods give reproducible results.

Presently, the titanium components are made in the following manner. First, there is a monitored machining using computer-controlled workshop machines. The machines include cutting tools. This machining gives a surface having microscopic irregularities.

During the machining with the cutting tools, oxidation of the workpiece takes place. The oxidation causes formation of titanium oxides. The machining also promotes the formation of a biologically correct micro-cratered, moon-surface-type surface structure, in accordance with the above-mentioned patent.

After the machining, the components are burred and inspected. After that, the surface is cleaned by means of a number of washing steps in different liquids. The washed components are then packed manually in glass ampoules. The ampoules are sealed hermetically by fusing with the aid of a flame. The content of the glass ampoule is then heat-sterilized, after which the sterile package is packed in a so-called blister pack made of plastic. The blister packs are then also sterilized, after which they are packed in cardboard boxes.

During the machining, a thin, approximately 2–3 nm oxide layer is formed on the titanium. A characteristic surface structure is also formed on the titanium. The oxide layer and the surface structure are judged to be pre-requisites for successful osseointegration. However, the surfaces of the components also become covered with a layer of impurities. The impurities principally include residues from cutting liquids that are removed in the subsequent washing stages. During the sterilization in the glass ampoule, the thickness of the oxide layer increases to the final value, which is 4–6 nm.

Those surfaces of the finished titanium component (the implant) that come into contact with the biological tissue consist, consequently, of a thin titanium oxide layer ($TiO_2$) that is covered with a contamination layer. The latter consists in the main of adsorbed hydrocarbons from the air, etc., and trace quantities of other, inorganic, substances. The exact composition of the contamination layer is a complex function of the whole history of the preparation of the implant. It is desirable that this contamination layer be removed at the same time as the characteristic surface structure is retained, since only this surface structure has been found to give clinical results.

The object of the present invention is to control the characteristics and reproducibility of the surface structure of the titanium component to an even higher degree than present employed methods. The intention is to prepare the surface so that existing surface contaminants and the oxide layer are removed. In other words, the invention erases the "memory" from preceding preparation steps. Then the desired surface is prepared in a well-controlled manner in a controlled environment.

In accordance with the invention, the surface of the implant is prepared using a gas-discharge plasma, a called glow discharge.

The reason for using this type of surface preparation is that, when utilized correctly, it permits a superior degree of control, reproducibility and flexibility in the manufacturing procedure as compared with a conventional preparation. This assessment is based partly on experiences from other areas of technology in which plasma and other vacuum-based preparation methods are used in the production. In this context, the most conspicuous example is the manufacture of semiconductor components. The achievable high-grade process control results from the fact that vacuum methods are very clean and that they can be carried out in closed systems without being affected by uncontrolled environmental atmospheres. Apart from that which has been stated above, the assessment is also based on straightforward fundamental considerations regarding the advantages of a closed vacuum process, and, additionally, on our own experiments described below.

The principle of using plasma for preparing surfaces can be described simply with the aid of FIG. 1, which diagrammatically illustrates a plasma reactor (vacuum chamber). The gas-discharge plasma 1 is generated by a high voltage (about 1 kV) being applied across a gas between two electrodes under a low pressure (~0.01–100 m Torr). The two electrodes can be constituted by the sample and the vacuum chamber itself, as in the FIG. 1. The relatively high electrical field results in the few free electrons, which are always present, being accelerated up to energies that are sufficient to ionize the gas molecules that they collide with. This releases further electrons that, in turn, are accelerated and ionize further gas molecules, etc. The ionized molecules will, in turn, be accelerated by the electrical field and collide with gas molecules, which become ionized, and with the surfaces in the system. Both the ionizing events and the ion-surface collisions create new free electrons, thereby bringing about a "cascade effect", resulting in the degree of ionization of the gas being greatly increased. Finally, an equilibrium is established in which a stable current, due to transport of ions and electrons, flows through the gas. This "controlled" gas discharge is a plasma, and is often called a "glow discharge" since it emits visible light as a consequence of the physical processes that are taking place in it. In the following description, the term plasma is used. Use of the term plasma must not, however, be confused with the type of hot plasmas which are found, for example, in stars, where the degree of ionization and the temperature are much higher.

The temperature in a gas-discharge plasma is insignificantly higher than the environmental temperature. In addition to neutral gas molecules, free electrons and ionized gas molecules, the plasma also contains free radicals, metastable conditions and other reactive components. These have a much higher tendency to react with, for example, a surface than do unionized and nonexcited molecules.

Depending on a number of different process parameters, for example, DC or AC voltage, electrode configuration and geometrical design, process gas and pressure, among others, a large number of different effects can be produced on the sample surface using the plasma. Most of these applications principally utilize the effects that arise when the electrode surfaces are bombarded with high-energy ions in the plasma.

In this context, some important processes are:

(i) Sputtering, which entails the high-energy ions knocking off surface atoms from the surface. This effect can be used for mild (dry) cleaning/sterilizing or for finishing/etching surfaces, among other things.

(ii) Surface reactions between ions and surface, entailing some of the bombarding ions reacting chemically with the surface and forming a layer possessing a new chemical composition. The fact that some of the gas molecules are present in ionized or excited conditions makes them, as a rule, more reactive than corresponding neutral molecules. By varying the type of ions, that is, the process gas, oxide layers, nitride layers or carbide layers can be made, for example.

(iii) Implantation of ions, that is, with some of the incoming ions penetrating the surface layer of the sample and becoming embedded in it. Here too, chemical modifications of the surface layer can be produced.

(iv) "Activation" of the surface. The ion bombardment breaks bonds in the surface, thereby making the latter especially inclined to react with, or bind to, molecules from the environment. This is often termed giving the surface a high degree of surface energy.

(v) As a rule, structural changes arise at various levels. These can be defects at the atomic level, changes in microstructure, or even modified surface topography and morphology.

The abovementioned effects occur to different extents and are associated with each other. By varying the process parameters, the processes which are to dominate can, to a certain extent, be selected. In other words, the plasma technique is a very versatile method for treating surfaces. The method can also advantageously be combined with a variety of subsequent surface-treatment steps in the same chamber in which the plasma treatment takes place.

In principle, preparing or modifying (cleaning, sterilizing, oxidizing, nitrating, etc.) implant surfaces using gas-discharge plasma is not novel. The method was proposed and tested as early as the 1970's by Baier, among others. In recent years, the method has caused greatly increased interest in relation to implants. For example, and the use of a gas-discharge plasma for cleaning dental titanium fixtures, for example, has been proposed in U.S. Pat. No. 5,071,351.

"Plasma cleaning and related treatments" is also described in J. Biomed. Mater. Res.: Applied Biomaterials, Vol 22, No. A2, 145–158 (1988), Bengt Kasemo and Jukka Lausmaa "Biomaterial and implant surfaces: On the role of cleanliness, contamination, and preparation procedures" on pages 152–153.

However, in those instances in which plasma preparation has been used in connection with implants, the potential of the method has not been exploited to the full. The reason for this is as follows:

During plasma preparation, a reactive surface having high so-called surface energy is formed as a rule. This means that the surface has a strong tendency to bind that itself molecules from the surrounding atmospheres to it is exposed to. In most instances in which plasma preparation has been applied to implant surfaces, conventional and/or commercial plasma equipment has been used. After completion of the plasma treatment, the plasma-prepared surface is exposed to uncontrolled atmospheres, signifying that the properties of the plasma-prepared surface can be lost. The contaminating molecules that become bound to the surface are often different types of hydrocarbons and other volatile organic molecules. As an example of how rapidly this contamination takes place, it can be mentioned that at a concentration of a contaminant in the air of 1 ppb ($10^{-9}$) a monolayer of contaminating molecules can be bound to the surface in ~1s. In the case of ppm concentrations, the corresponding time scale is ~1 ms.

Apart from the plasma-prepared surface, in the case of previous commercial plasma equipment, having been exposed to uncontrolled atmospheres after the treatment, the plasma equipment has not been adapted, as far as implants are concerned, to production-scale conditions. Thus, the Harrick Scientific chamber which is described in U.S. Pat. No. 5,071,351 is not suitable when a relatively large number of titanium components are to be prepared during production. For example, divergences in the properties can occur if several implants are being treated simultaneously, due to variations in the different geometrical positions of the plasma in the plasma chamber.

SUMMARY OF THE INVENTION

The object of this invention is to develop a method for preparing implant surfaces, preferably made of titanium, using a gas-discharge plasma, where the equipment and the process parameters have been adapted for large-scale production. At the same time, it is required of the plasma process that the surface properties of the finished product, with regard to chemical composition, oxide thickness and structure, should come within the predetermined characteristics. However, the divergence between individual samples and between different sample batches should be less than in the case of current production. In addition, the process should not introduce new surface contaminants.

The plasma process should, in addition, be such that the macroscopic appearance of the surface and the microstructure, of topography, of the surface within the interval 10–1000 nm are not altered by the process. In addition, in those instances in which the process includes ampoule sealing, all the components in the pack, and the total final result, should satisfy the official requirements for sterility that are in force.

The invention is based, in this context, on a closed system concept in which the plasma preparation and, where appropriate, the remaining preparation steps, and, where appropriate, the packaging and transport to biological environments, as well, are carried out in accordance with a closed procedure without intermediate exposure to uncontrolled environmental atmospheres. This approach has the very great advantages, as compared with existing processes, of achieving a very high grade of controlled surface structure and reproducibility and of preserving the properties of the plasma-prepared surface right up to the moment of use.

In accordance with the invention, the implants are conveyed, after customary machining and any washing procedures that may be necessary, to a vacuum chamber in which the plasma preparation is carried out in two steps. The first step includes treatment with an inert gas plasma so that existing surface contamination layers and oxide layers are removed from the implant surface. Then, a reoxidation step is performed, using an oxidizing plasma or by means of thermal oxidation. The plasma preparation, and any remaining preparation steps that may be necessary, and handling of the implants are carried out in accordance with a closed procedure without intermediate exposure to uncontrolled environmental atmospheres.

The high-vacuum chamber, the preparation chamber, must have a vacuum performance that corresponds to the stipulated requirements for purity and control in the process. Preferably, the basal pressure should be below $10^{-6}$ mbar. The plasma process pressure is in the mbar range, except in the case of the thermal oxidation in $O_2$, when the pressure can be higher, in the 10–1000 mbar range.

In a first embodiment, the plasma treatment, cleaning and oxidation, complements or replaces a part of the present cleaning, that is, as a last step before sealing and sterilizing in glass ampoules is carried out.

Alternatively, the plasma treatment can be coupled together with sterilizing and sealing in glass ampoules. This involves all the steps from final cleaning to sterilization and sealing in glass ampoules being carried out in a closed vacuum system without intermediate exposure to environmental or other uncontrolled atmospheres.

BRIEF DESCRIPTION OF THE DRAWINGS

In that which follows, the invention will be described in more detail in association with the enclosed drawings, which show some examples of how the invention can be applied.

FIG. 5 shows a detail of a cathode and sample holder, and FIG. 6 shows the principle involved in scaling up the preparation of several samples of titanium components by multiplying the number of plasma cells.

DETAILED DESCRIPTION OF THE INVENTION

Figure 1:
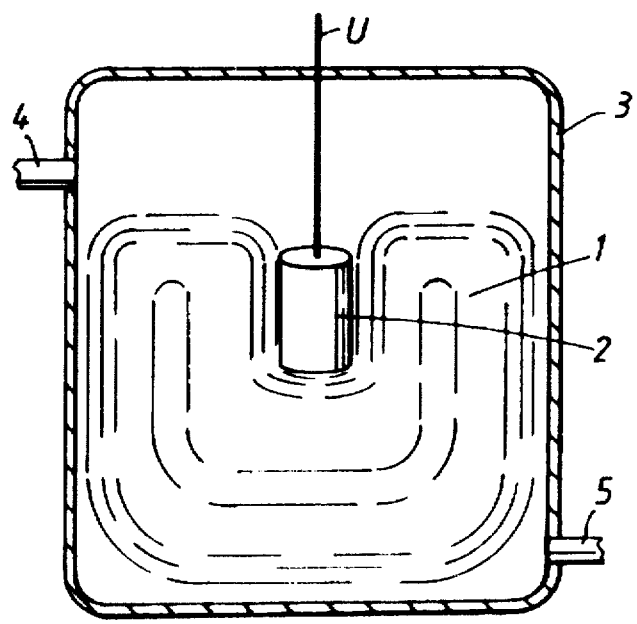
FIG. 1 diagrammatically illustrates a conventional vacuum chamber for plasma treatment, FIG. 2 diagrammatically shows two alternatives for carrying out plasma treatment of titanium implants.

The principle of plasma preparation of surfaces has already been described in the introduction in conjunction with FIG. 1. The gas-discharge plasma 1 is generated by applying a high voltage across the gas under a low pressure. The two electrodes are constituted by the sample 2 (the titanium component) and the wall 3 of the vacuum chamber. The vacuum chamber is provided with a gas inlet 4 and a gas outlet to a pump 5.

Figure 2:
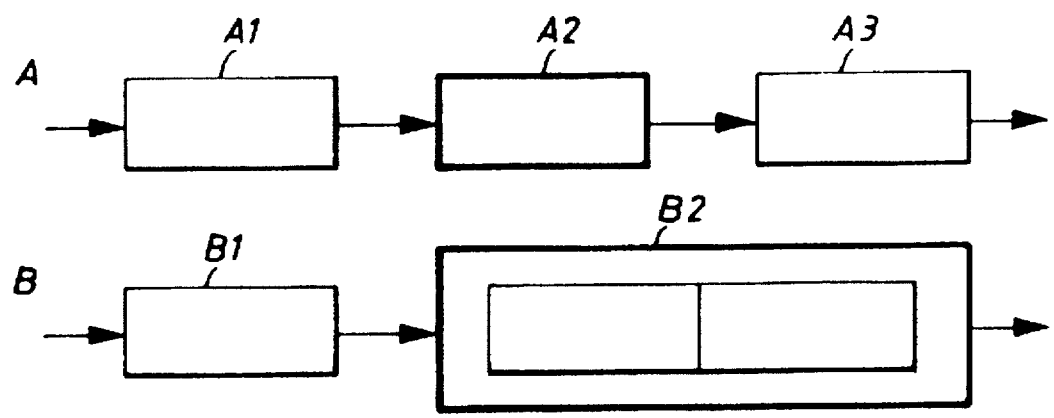

FIG. 2 shows how the plasma treatment of titanium components can be applied under production-scale conditions.

Figure 3:
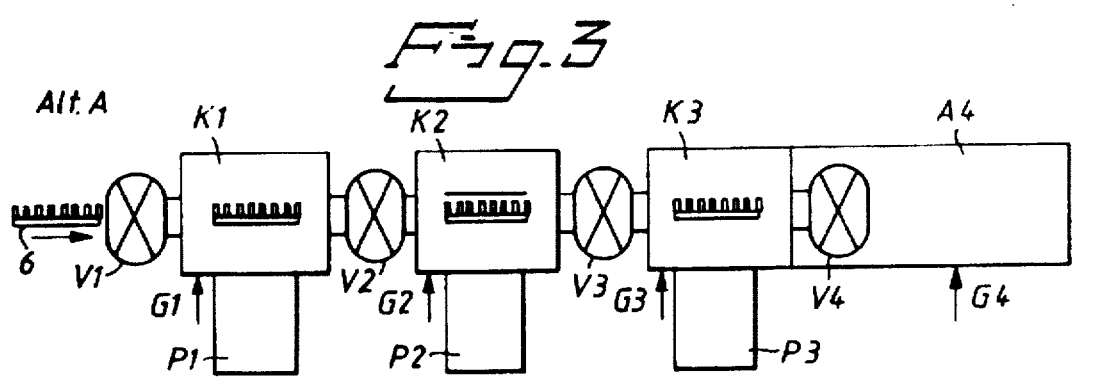
FIG. 3 shows the principle of equipment for closed plasma treatment under production-scale conditions, where Alternative A shows the case in which the plasma-treatment equipment is coupled to a closed space possessing a controlled atmosphere and in which sterile packaging takes place, for example a called glove box, or a sterile bench. Alternative B shows the case in which sterilization and packaging have been incorporated into the plasma equipment.

In accordance with Alternative A, shown in FIG. 3 and including components A1, A2, and A3, plasma treatment A2 is introduced after machining and washing procedures A1 (cleaning and oxidation) as a complement to, or replacement for, the previously effected cleaning. In other words, the plasma treatment is a last step before mounting, sealing and sterilizing A3 in glass ampoules.

In accordance with Alternative B, shown in FIG. 3 and including components B1 and B2, sterilization, mounting and sealing in glass ampoules are incorporated into the system for plasma treatment. This involves carrying out final cleaning, sterilization and sealing in glass ampoules in a closed vacuum system without any intermediate exposure to uncontrolled environmental atmospheres.

Between Alternative A and Alternative B, there are a number of "intermediate levels", depending on how the sample transport between plasma treatment and sterile packaging is effected. For example, Alternative A above could be coupled together with glass ampoule sealing in a controlled atmosphere, in a so-called glove box filled with synthetic air or other suitable gas.

In the subsequent description, it is assumed that a closed procedure is being used, that is, Alternative A combined with sterile packaging in a controlled atmosphere, or Alternative B.

The plasma treatment consists principally of two steps. In the first step, the outermost $\leq 10$ nm of the sample surface are removed using an inert gas plasma. The surface is then reoxidized, either thermally or using an oxidizing plasma, for example, $O_2$, in such a way that the desirable oxide layer is obtained. In order to produce further surface modifications, other process gases can be used, such as, for example, $N_2$ (nitridation), $H_2O$, (hydroxylation), $H_2O_2$, $SO_4/PO_4$, ions (doping) and monomers (polymer coatings). Suitable process parameters for cleaning and oxidation can, for example, be:

Cleaning: pure (>99.999%) argon gas; 0.5–3 kV negative direct current voltage on the sample; ~0.1–0.5 mbar Ar pressure; 0.01–0.1 mbarl s$^{-1}$ Ar flow; resulting in plasma currents of ~0.5–2 mA cm$^{-2}$ sample surface; for 0.5–20 minutes.

Oxidation: thermal oxidation in 1–1000 mbar pure (>99.99%) $O_2$ at room temperature for 10 min., alternatively $O_2$ plasma (0.2–3 kV negative direct current voltage on the sample; 0.01–0.5 mbar $O_2$ pressure; 0.01–0.1 mbarl s$^{-1}$ $O_2$ flow; resulting in plasma currents of ~0.5–50 mA cm$^{-2}$ sample surface; for 0.5–20 minutes).

The preparation can also advantageously be effected in a combined process by gradually introducing oxidizing gas into the process gas (for example mixing $O_2$ into Ar) during the final phase of the cleaning.

Since the plasma treatment is carried out in a near vacuum pressure $10^{-1}$–$10^{-3}$ mbar, the equipment for plasma treatment consists in principle, of a vacuum system with components that are necessary for the plasma process and that are vacuum-compatible. From the point of view of cleanliness, it is advantageous if the vacuum system consists of separate chambers that are coupled together via valves and between which the samples can be transferred without the vacuum being broken. The principle of equipment for closed plasma preparation in accordance with the two alternatives is shown diagrammatically in FIG. 3.

The two alternatives have in common:

1. A vacuum chamber (K1) whose function is to sluice the sample into the plasma preparation chamber (K2). Vacuum chamber K1 is accessible from the atmosphere via a valve V1, and is also coupled to vacuum chamber K2 via valve V2. If required, vacuum chamber K1 can also be coupled to a gas inlet G1 for flushing gas, in order to maintain a higher degree of cleanliness.

2. A vacuum chamber (K2), in which the plasma preparation, and any other preparation steps, for example oxidation or heat-sterilization, which may be necessary, takes place. The plasma chamber contains components that are suitable for the process, for example a plasma electrode, electrical connections, process gas inlet G2, pressure or flow regulating systems, P1, P2, P3, P4, etc. The vacuum requirements for this chamber must satisfy the requirements that are stipulated by the plasma process (described below). Due to the fact that a sluicing system is used, this chamber is never exposed to air, except during maintenance work, and, as a result, can be maintained at a high degree of cleanliness.

3. A vacuum chamber (K3) that functions as a sluice for discharging the plasma-prepared samples through the valve V4. Vacuum chamber K3 is coupled to the preparation chamber via valve V3. Vacuum chamber K3 includes gas inlet G3 the system is assembled linearly, the process takes place continuously. In other words, new samples are conveyed into vacuum chamber K1 while a set of samples is plasma-prepared in vacuum chamber K2, and so on. If a continuous process is not required, valve V3, vacuum chamber K3 and valve V4 can be dispensed with. Vacuum chamber K1 then functions as a sample sluice both for conveying in and out the samples. Vacuum chamber K3 and valve V3 can also be dispensed with if valve V4 is coupled to vacuum chamber K1, although in a different direction as compared to valve V1.

The implants are expediently conveyed into the system mounted on a cassette or the like 6 (described below), thereby allowing several samples to be treated on each occasion. The cassette is then conveyed between the different chambers through the valves using an appropriate transport system. Depending on which of the alternatives A and B is under consideration, the following system components are also additionally required:

(A)4. In order that a closed process can be effected, the discharge sluice (K3, V4) is coupled directly to a closed space in which a controlled and, where appropriate, sterile, atmosphere (vacuum, atmospheric pressure or excess pressure) can be maintained. In this volume, sterile packaging and, where appropriate, sterilization, are effected either manually or automatically. This space can be, for example, a so-called glove box that satisfies necessary requirements for sterility. In addition to sterile packaging, a multiplicity of components and functions can advantageously be incorporated into this space. These components and functions can include, for example, UV irradiation for cleaning/sterilizing, admission of a suitable gas atmosphere, and analytical equipment. The analytical equipment can include, for example, a mass spectrometer, for monitoring the gas composition in the space and, thus, also the sterile packaging. It should also be possible to carry out any necessary further preparations of the implant surface in this space under atmospheric pressure or in a liquid.

(B)4. Where the sterile packaging step is carried out in the vacuum system, a chamber (K3) and a valve (V3), which is expediently situated between the plasma-preparation chamber and the discharge sluice, are additionally required. This chamber contains the necessary components for carrying out the sterile packaging. These components can include manipulators, supply of components for the packaging, equipment for sealing the packaging material, among others.

Alternative A shown in FIG. 3 includes another component A4 that includes a gas inlet G4. Also, Alternative B shown in FIG. 3 includes vacuum chamber K4 and valve V5.

Figure 4:
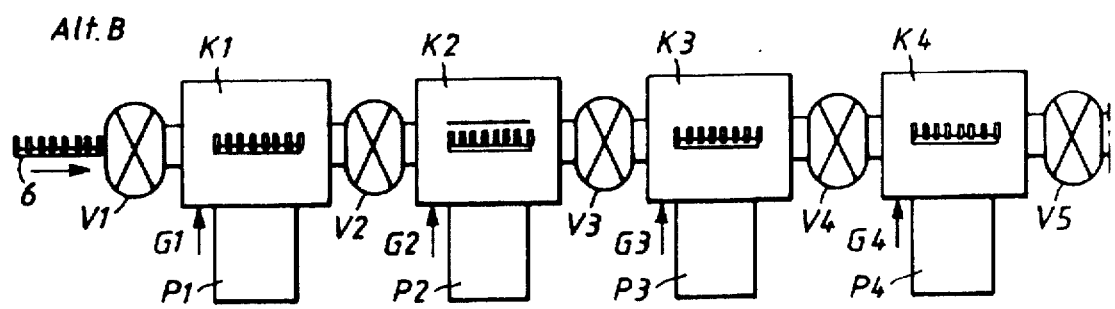
FIG. 4 is a diagrammatic sketch of the plasma cell itself.
Figure 4:
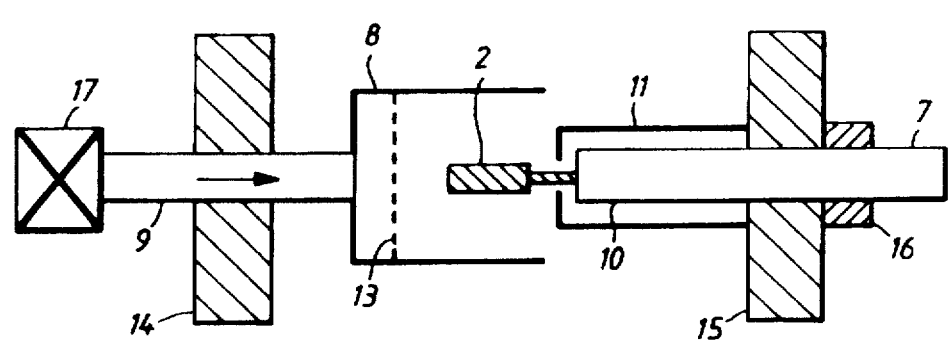

Each sample (titanium component) 2 is plasma-prepared individually in a local plasma cell, shown in FIGS. 4 and 5. In the cell, in which the sample constitutes the cathode, by being coupled to negative high voltage or to an alternating high current voltage 7. A hollow cylinder 8 around the sample functions as the anode. The anode is normally grounded. The plasma cell can also advantageously function as the local gas inlet 9 around the sample, as shown in FIG. 4. A construction of this type means that the flow of process gas around the sample can be effectively controlled, that the influence of any impurities in the residual gas in the preparation chamber can be minimized, and that a certain cooling effect on the sample can be brought about. The geometry of the cell ensures that the gas-discharge plasma is delimited around the sample. The geometry of the anode can be adapted in a suitable manner for non-cylindrical samples. This local arrangement allows simple scaling-up using a number of identical plasma cells, with gas flows and plasma conditions otherwise being identical.

The sample 2 is mounted on a cathode rod 10, which is electrically shielded by a grounded shield 11. This arrangement eliminates discharges outside the cell. In order to avoid short circuits between the grounded shield and the cathode, insulating material 12 is applied at appropriate sites, as shown in FIG. 5. In order to minimize the risk of contaminants from the cell, all the components which the sample surface "sees" should be manufactured in the same material as the sample. The titanium grating 13 on the gas inlet has the function of delimiting the plasma and of eliminating contaminants from the material used for manufacturing the gas inlet.

Besides this, FIG. 4 shows two vacuum flanges 14 and 15 with gas inlet and electrically insulating vacuum lead-through 16 for the high voltage, respectively. A pressure or flow regulator 17 regulates the gas supply.

FIG. 5 shows the cathode 10 and the sample holder in more detail. The cathode is cylindrical and has a narrow projecting threaded part 18 onto which the titanium component, for example a fixture, is screwed. The cathode has a core 19 of titanium that extends out into the narrower, threaded part 18 that is entirely executed in titanium. The outer part 20 of the cathode is made of copper. The insulating material can be a ceramic sleeve 21, for example made of $Al_2O_3$, and a BN insulator 22.

FIG. 6 shows how a multiplicity of titanium components (samples) 2 can be plasma-treated simultaneously by the number of plasma cells being multiplied. Under these circumstances, a matrix of identical cells is assembled whose gas supply is effected by a "branched pipe" 23. The conditions in each individual cell are then identical with that described above for one cell. A large number of samples can thereby be treated simultaneously under identical conditions, permitting high production capacity.

We claim:

1. A method for preparing surfaces of implants using gas discharge plasma, said method comprising the steps of:
   1) conveying the implants to a vacuum chamber;
   2) treating the implants in the vacuum chamber with an inert gas plasma, to remove existing surface contamination and oxidized layers of material that the implant is formed of from the implant surfaces; and
   3) treating the implants in the vacuum chamber with an oxidizing plasma or by thermal oxidation, to reoxidize the implant material at the surfaces of the implants;
   wherein said vacuum chamber is a closed space, including a controlled atmosphere to produce a highly accurate and reproducible microstructure, composition, purity, and sterility in said implants.

2. A method according to claim 1, further comprising modifying the implant surfaces by introducing gasses into said vacuum chamber during said reoxidation of the implant surfaces, said gasses including at least one member selected from the group consisting of $N_2$, $H_2O$, $H_2O_2$, $SO_4/PO_4$, ions, and monomers.

3. A method according to claim 1, wherein said oxidizing plasma is $O_2$ plasma.

4. A method according to claim 1, further comprising the steps of:
   machining the implants; and
   washing the implants;
   wherein said machining and washing steps are carried out prior to conveying the implants into the vacuum chamber.

5. A method according to claim 1, wherein said implants are made of metallic or ceramic material.

6. A method according to claim 1, wherein said implants are titanium.

7. A method according to claim 1, further comprising the steps of:
   mounting said implants in ampoules;
   sealing said ampoules; and
   sterilized said ampoules;
   wherein said mounting, sealing, and sterilizing steps are carried out after said treating steps and are carried out in a closed space, including a controlled atmosphere, without exposure to an uncontrolled atmosphere.

8. A method according to claim 1, further comprising the steps of:
   mounting a plurality of implants on a cassette; and
   conveying said cassette into the vacuum chamber, thereby simultaneously preparing a plurality of implants.

9. A method according to claim 8, further comprising the steps of:
   providing at least one sample sluice;
   coupling said at least one sample sluice to the vacuum chamber via at least one valve; and
   conveying said cassette into and out of the vacuum chamber for plasma treating via the at least one sample sluice.

10. A method according to claim 9, wherein said at least one sample sluice is a vacuum chamber.

11. A method for preparing surfaces of implants using gas discharge plasma, said method comprising the steps of:
    1) conveying the implants to a vacuum chamber;
    2) treating the implants in the vacuum chamber with an inert gas plasma to remove from the implant surfaces existing surface contamination and a layer comprised of oxidized material, the oxidized material being an oxide of material from which the implant is formed;
    3) treating the implants in the vacuum chamber with an oxidizing plasma or by thermal oxidation, to reoxidize the implant material at the surfaces of the implants; and
    4) modifying the implant surfaces by introducing gasses into said vacuum chamber, said gasses including at least one member selected from the group consisting of $N_2$, $H_2O$, $H_2O_2$, $SO_4/PO_4$, ions, and monomers;
    wherein said implant treating steps 2 and 3 are carried out in a closed, controlled atmosphere to produce a highly accurate and reproducible microstructure, composition, purity, and sterility in said implants.

12. A device for preparing surfaces of implants using gas discharge plasma, comprising:
    a first vacuum chamber including at least one plasma cell for treating an implant;
    a source of high negative voltage providing a cathode of said at least one plasma cell and connected to said implant;
    a body comprising a hollow cylinder essentially surrounding said implant and providing an anode of said at least one plasma cell, said body having a geometry adapted to the shape of said implant, and providing a local gas inlet around said implant;
    means for treating the implants with an inert gas plasma to remove existing surface contamination and oxide layers from the implant surface;
    means for treating the implant surfaces with an oxidizing plasma or thermal oxidation to reoxidize the implant surfaces; and
    a closed space including a controlled atmosphere and the first vacuum chamber, said closed space producing a highly accurate and reproducible microstructure, composition, purity, and sterility in said implants.

13. A device according to claim 12, further comprising:
    a plurality of vacuum chambers including said first vacuum chamber; and
    a plurality of valves for coupling together said plurality of vacuum chambers;
    wherein the implants may be transferred among the vacuum chambers without breaking a vacuum in the vacuum chambers.

14. A device according to claim 13, further comprising:
a cassette for receiving a plurality of implants; and
a transport system for conveying said cassette among said plurality of vacuum chambers via said plurality of valves.

15. A device according to claim 12, wherein said implant is mounted on a cathode rod that is electrically shielded by a grounded shield that eliminates discharges outside the at least one plasma cell.

16. A device according to claim 12, wherein said at least one plasma cell includes titanium surfaces that face said implant.

17. A device according to claim 16, wherein a titanium anode grating is arranged in said gas inlet for delimiting plasma in said at least one plasma cell and for eliminating contaminants from a material from which the gas inlet is manufactured.

18. A device according to claim 12, wherein said first vacuum chamber includes a matrix of identical plasma cells each for preparing one implant, and a branched pipe positioned and arranged so as to supply inert gas to each said plasma cell.

19. A device according to claim 12, wherein said inert gas plasma comprises argon gas, said argon gas plasma is at a plasma process pressure of from 0.1–0.5 mbar, and reoxidation of said implant surfaces is carried out in $O_2$ plasma at a pressure of 0.01–0.5 mbar or by thermal oxidation in $O_2$ gas at a pressure of 1–1000 mbar.

20. A device according to claim 12, further comprising an apparatus for mounting the implants in ampoules, sealing the ampoules, and sterilizing the ampoules.

21. A device according to claim 12, further comprising at least one sample sluice and at least one valve for connecting said at least one sample sluice to said first vacuum chamber, wherein said at least one sample sluice is a vacuum chamber.

* * * * *